(12) United States Patent
Sonnenschein et al.

(10) Patent No.: US 6,997,871 B2
(45) Date of Patent: Feb. 14, 2006

(54) MULTIPLE VIEW ENDOSCOPES

(75) Inventors: Elazar Sonnenschein, Beer Sheva (IL); Minelu Sonnenschein, Meitar (IL); Randal B Chinnock, Sturbridge, MA (US)

(73) Assignee: Medigus Ltd., (IL)

( * ) Notice: Subject to any disclaimer, the term of this patent is extended or adjusted under 35 U.S.C. 154(b) by 36 days.

(21) Appl. No.: 10/030,016

(22) PCT Filed: Sep. 6, 2001

(86) PCT No.: PCT/IL01/00843

§ 371 (c)(1),
(2), (4) Date: Feb. 20, 2003

(87) PCT Pub. No.: WO02/24058

PCT Pub. Date: Mar. 28, 2002

(65) Prior Publication Data

US 2003/0163029 A1    Aug. 28, 2003

(30) Foreign Application Priority Data

Sep. 21, 2000 (IL) ..................................... 138632

(51) Int. Cl.
*A61B 1/005* (2006.01)
(52) U.S. Cl. .................. 600/173; 600/129; 600/166
(58) Field of Classification Search ............... 600/113, 600/166, 111, 129, 171, 170, 176, 173
See application file for complete search history.

(56) References Cited

U.S. PATENT DOCUMENTS

| | | | |
|---|---|---|---|
| 3,889,662 A | 6/1975 | Mitsui ........................ 128/6 |
| 4,872,740 A * | 10/1989 | Terada et al. ............... 385/117 |
| 5,166,787 A | 11/1992 | Irion ........................... 358/98 |
| 5,609,561 A * | 3/1997 | Uehara et al. ............... 600/112 |
| 5,693,968 A * | 12/1997 | Cherry et al. ............... 257/231 |
| 5,776,049 A | 7/1998 | Takahashi .................... 600/111 |
| 5,871,440 A * | 2/1999 | Okada ......................... 600/129 |
| 5,929,901 A * | 7/1999 | Adair et al. ................... 348/76 |
| 5,976,076 A * | 11/1999 | Kolff et al. .................. 600/166 |
| 6,059,719 A * | 5/2000 | Yamamoto et al. .......... 600/127 |
| 6,159,146 A * | 12/2000 | El Gazayerli ................ 600/106 |
| 6,387,043 B1 * | 5/2002 | Yoon ........................... 600/109 |
| 6,547,723 B1 * | 4/2003 | Ouchi .......................... 600/146 |
| 2002/0007110 A1 | 1/2002 | Irion ........................... 600/170 |
| 2003/0171651 A1 * | 9/2003 | Page et al. ................... 600/127 |
| 2003/0220657 A1 * | 11/2003 | Adams ........................ 606/139 |
| 2004/0010271 A1 * | 1/2004 | Kortenbach ................. 606/139 |

FOREIGN PATENT DOCUMENTS

WO          8911252         11/1989

* cited by examiner

*Primary Examiner*—John P. Leubecker

(74) *Attorney, Agent, or Firm*—Baker Botts L.L.P.

(57) ABSTRACT

An endoscope comprises a sheath, an articulation section adjacent to its distal tip, and two or more separate optical channels that produce two or more distinct views. Each of the optical channels comprises an objective lens and a means of capturing and/or viewing the image. The objective lens or lenses of the optical channel that produces the first distinct view, is located at a first location on the distal tip. The objective lens or lenses of the optical channel that produces the second distinct view is located at a second location on the proximal end of the articulation section or on the sheath of the endoscope adjacent to or located proximally of the articulation section.

12 Claims, 17 Drawing Sheets

MULTIPLE VIEW ENDOSCOPES

FIELD OF THE INVENTION

The invention applies to the field of endoscopy. More specifically the invention provides an endoscope with two or more optical channels that produce two or more distinct views.

BACKGROUND OF THE INVENTION

GastroEsophageal Reflux Disease (GERD) is a common medical condition that affects approximately 44% of the US adult population to some degree. GERD symptoms are currently the most common reason that patients visit a gastroenterologist. The lower esophageal sphincter is a one-way valve that normally prevents stomach acids from entering the esophagus. Failure of the lower esophageal sphincter allows stomach acid to reflux upwards into the lower esophagus, typically after meals when the stomach is full and exerts greater pressure on the lower esophageal sphincter. Strong stomach acids will burn the delicate lining of the esophagus, causing "heartburn" or "acid indigestion" to occur. Heartburn is experienced as a burning or pressure sensation behind the breastbone, and can be accompanied by foul-tasting regurgitation into the back of the throat. Recurrent heartburn will damage the esophagus over time, and can lead to more serious conditions, including a cancer of the esophagus known as "Adenocarcinoma of the Gastroesophageal Cardia". Incidence of this particular type of cancer is rising in America and elsewhere.

Around 65 million Americans experience heartburn on a regular basis. The symptoms are uncomfortable, and most will seek some form of treatment. Options for treatment of acid reflux range from over-the-counter remedies and behavior modification (such as sitting up after meals or avoiding certain foods) to prescription drugs and surgery. Medications treat the symptoms of GERD, but do nothing to remedy the underlying cause. Drug treatments function by shielding the esophageal tissues for a period of time, stimulating their healing, or by suppressing stomach acid formation. All produce temporary effects and must be consumed on a regular basis. If the drugs are not taken, symptoms will very likely reoccur.

Surgical treatments are usually effective at eliminating the cause of acid reflux, and can be either open-incision or endoscopic (minimally invasive). The surgical procedure is designed to create a new functional lower esophageal sphincter or repair the damaged lower esophageal sphincter and thus prevent GERD. The most common surgical solution is to perform some variation of a procedure named "fundoplication". This surgery involves wrapping the fundus (upper body) of the stomach around the lower esophagus, which causes compression of the lower esophagus when the stomach is loaded with food. This effectively prevents acid reflux. The wrap of the fundus around the esophagus may be 360 degrees or less. More complete wraps are associated with inability or difficulty in belching or vomiting. Partial fundoplications are therefore the preferred variation of this surgery. Fundoplications may be performed in an open procedure, or using an endoscope with a percutaneous approach (inserting the endoscope through one or more incisions in the abdomen).

Very recently, trans-oral endoscopic procedures have been developed for surgical treatment of GERD. One procedure involves constricting the lower esophageal sphincter by suturing. Another procedure involves constricting the sphincter by injecting a material into the surrounding tissues to "fatten them up". Yet another procedure involves applying sufficient heat to surrounding tissues to stiffen them.

In copending International patent application PCT/IL01/00238 by the same applicant hereof, the description of which is incorporated herein by reference, there is described an endoscopic apparatus and procedure for performing partial fundoplications that provides an alternative to all of the above-mentioned options for the treatment of GERD.

Endoscopy is a mature class of surgery that came into wide use after the invention of the Hopkins "rod-lens" relay system in the 1960s. Prior to this breakthrough, endoscopes provided very poor image quality coupled with an inability to provide and transmit adequate illumination and were not suitable for most surgical and diagnostic applications. An endoscope is an optical instrument used to visualize the interior of the human body, through natural or surgical openings. The advantages of endoscopic procedures include less trauma to the patient, shorter (or no) hospital stay, less pain, faster healing, and generally lower cost per procedure. The advantages of open surgery include greater ability for the physician to see and manipulate structures. The earliest endoscopes relied on the physician to directly view the interior surgical site by looking through the eyepiece of the endoscope. As video camera technology evolved, endoscopes could be coupled to a video camera indirectly through a coupling lens attached to the eyepiece, or directly by coupling the image to the sensor without use of an eyepiece at all. The use of video displays allows the entire operating team to view the surgical site, and the surgeon is not required to keep his eye at the endoscope ocular. The use of video also permits documentation (image storage) without the use of bulky and inconvenient photographic equipment.

Endoscopes currently exist in an array of different forms and are suitable for a wide variety of surgical procedures. Most endoscopes are designed to provide a broad view of the interior surgical site, but do not necessarily provide adequate visualization of the tools used with the endoscope. Even though endoscopes may be highly specialized for a particular procedure, they all contain the same basic component systems. An objective optical system captures a single image or view of the surgical area, a relay optical system carries the image from the distal to proximal end of the device, and an eyepiece or camera system (or both) are used to view the transmitted image. Light to illuminate the surgical scene is delivered via optical fibers or waveguides that are integral to the endoscope. The endoscope may also contain working channels or incorporate treatment options such as laser delivery. All of these parts are contained within an outer sheath that may be made from rigid or flexible materials. The endoscope itself may be rigid, semi-flexible, or flexible, and may have the ability to actively bend in one or more directions at its distal tip.

The objective of an endoscope may consist of glass or plastic lenses, diffractive or hybrid diffractive/refractive lenses, GRIN (graduated refractive index) lenses, prisms or mirrors. The image relay system may consist of a series of glass rods and lenses (a "rod lens" system), a series of lenses only, or fiberoptic image guides. The relay system may be bypassed in a video-only endoscope by placing the image sensor directly in the objective focal plane. The eyepiece typically consists of glass or plastic lenses. A video camera may be coupled to the eyepiece via a coupling lens, or may connect directly to the endoscope and view the image formed by the relay or objective system directly. A light source is coupled to the endoscope by a flexible fiberoptic cable in most cases, and is delivered by optical waveguides or fibers that may be glass or plastic. Some endoscopes provide viewing in stereo by incorporating more than one optical system at the proximal end to view the scene from two slightly offset perspectives. While these stereo endoscopes incorporate multiple image channels, they provide only one view of the surgical scene on an electronic display.

Endoscopes may be reusable or disposable, or may be split into one or more disposable and one or more reusable parts. Advantages of reusable endoscopes are that they are usually of much higher quality and have durability designed in. Disadvantages include degradation of the image quality after sterilization, which is performed using such methods as steam autoclave, ETO (ethylene oxide), glutaraldehyde, Steris (peractic acid), Sterrad (hydrogen peroxide plasma), or other harsh chemicals and temperatures. The sterilization process degrades optical coatings, cements, and surfaces, and can also have deleterious effects on the mechanical parts. Another disadvantage of reusable endoscopes is their comparatively high initial cost. Disposable endoscopes do not suffer from repeated sterilization, and also reduce the possibility of cross-contamination from one surgical procedure to the next. Because they must be purchased in larger quantities and do not need to be as durable, initial costs are less than reusables (though per-use costs are typically higher). Endoscopes that are partly disposable and partly reusable are designed to maximize the advantages of each type of device while minimizing the disadvantages and cost per use.

SUMMARY OF THE INVENTION

The present invention relates to an endoscope comprising two or more optical channels that produce two or more distinct views. The endoscope of the invention is suitable for performing various surgical procedures, including fundoplications, stapling of the stomach for obesity management, bladder neck sling procedures for incontinence management, and other procedures that may benefit from having multiple interior views. Such treatments may be performed percutaneously, or by gaining access via natural body canals such as the esophagus or urethra.

Thus, in one aspect, the invention is directed to an endoscope comprising two or more separate optical channels that produce two or more distinct views, each of said optical channels consisting of an objective lens and a means of capturing or viewing the image; each channel optionally also including one or more of the following elements: a) an optical relay system; b) an ocular; and c) a coupling lens suitable to deliver the image acquired by said objective lens to an image sensor and display apparatus; wherein each objective lens is located at a different position along the length of the endoscope.

In another aspect, the invention is directed to a GERD endoscope comprising:
 a) a sheath provided with a distal articulated section;
 b) stapler components distributed between a first location at the tip of said articulated section, and a second location along the length of said sheath, and which stapler components can be brought into a cooperative working positioned relationship by articulation of said articulating tip;
 c) a first objective lens located on said distal tip;
 d) a second objective lens located at said second location along the flexible sheath;
 e) a first optical channel to deliver the image acquired by said first objective lens to display apparatus coupled to said endoscope; and
 f) a second optical channel to deliver the image acquired by said second objective lens to display apparatus coupled to said endoscope.

In a further aspect, the invention is directed to a distal tip for a GERD endoscope comprising:
 a) a socket suitable to receive elements of a stapling device;
 b) at least one illumination channel; and
 c) at least one objective lens coupled to an optical relay system.

Each of the multiple views the endoscope produces has the following properties:
 The angle of the views may be between 0 to 180 degrees with respect to the mechanical axis of the endoscope.
 The field of view for each optical channel may be circular, with values up to 180 degrees or more.
 The field of view for each optical channel may be non-circular, such as square, rectangular, cylindrical, toroidal section, or other shape, or may be faceted, and may have an angular extent in each viewing axis of up to 180 degrees or more.
 For medical applications, the object viewed may be internal or external parts of human or animal bodies, parts of the endoscope, or surgical tools used in a procedure.
 For industrial applications, any object may be viewed, including parts of the endoscope and other tools used in the industrial procedure.
 The endoscope may operate in the visible, ultraviolet, infrared, or x-ray portions of the electromagnetic spectrum.

One or more of the following features may also be incorporated into the present invention:
 one or more image sensors to electronically acquire the views
 one or more displays to provide visual access to the electronically-acquired views
 one or more oculars to provide visual access to the views directly by the eye
 one or more of the image channels may provide stereoscopic imaging
 one or more portions that are disposable and one or more portions that are reusable
 one or more built-in functions (such as surgical staplers or laser delivery)
 one or more working channels for insertion of surgical instruments
 one or more illumination channels to provide adequate light for imaging or therapy such as photocuring or photoinitiation
 a rigid, semi-rigid, or flexible sheath, which may be disposable, resposable (multiple use disposable), or reusable
 active or passive articulation of the distal tip or an intermediate section in one or more axes Each of the optical channels includes one or more objective lenses and may include one or more relay optical systems. An objective lens forms an image of a scene. A relay optical system carries an image from one location in space to a different location in space. In an endoscope, the relay system is used to carry the image formed by the objective from the objective image plane to the focal plane of the sensor or ocular that is used to provide visual access to the image. The objective optical system may include elements such as mirrors, prisms, glass and plastic lenses that may be spherical or aspheric, GRIN lenses, diffractive lenses, hybrid diffractive/refractive lenses, fresnel lenses, other optical elements, filters, apertures, mechanical spacers, and lens housings. The optics in the objective may have a fixed focal length, variable focal length ("continuous zoom"), or multiple focal lengths ("step zoom", or "power changer"). The relay optical system may consist of mirrors, prisms, glass and plastic lenses that may be spherical or aspheric, gradient index lenses, diffractive lenses, hybrid diffractive/refractive lenses, fresnel lenses, fiberoptic image guides, optically transparent rods (such as glass or plastic), apertures, mechanical spacers, and housings.

The endoscope provides viewing via ocular(s), image sensor(s), or both. Oculars are generally glass or plastic lenses that are specially designed to work in conjunction with the optics in the human eye. They may be used in conjunction with an image sensor by the addition of coupling optics in between the sensor and the ocular. The construction of the ocular is not limited to glass and plastic lenses, and may be comprised of more exotic optical elements such as diffractive, gradient index, fresnel, or other types of lenses. The optics in the ocular may have a fixed focal length, variable focal length ("continuous zoom"), or multiple focal lengths ("step zoom", or "power changer"). The endoscope may include a method of actively focusing the ocular, objective, or sensor, or these components may be fixed-focus.

Image sensors are typically optoelectronic devices that convert photons into electrical signals. In the visible spectrum, charge coupled devices (CCD) or complementary metal oxide semiconductor (CMOS) sensors are typically used. In the infrared spectrum, silicon, or lead salt sensors are typically used. In the ultraviolet spectrum, doped silicon sensors are typically used. In the X-ray spectrum, a wavelength-converting device such as a microchannel fiberoptic plate is used in conjunction with a CCD sensor. When an image sensor is used, a separate display is necessary to provide access to the image presented to the sensor.

If an electronic sensor(s) is used, at least one display will be used to present the image to one or more members of the surgical team. Display types include cathode ray tubes, flat panel displays, head-mounted displays, and volumetric displays. This display may be separate, or it may be incorporated into the endoscope itself. Multiple views may be imaged on a single display, or multiple displays may be utilized to present one or more of the multiple views individually. If more than one view is presented on the same display, the views may be tiled or otherwise arranged on the screen simultaneously, or there may be an option to toggle between the views, which are displayed one at a time. Other information may be presented on one or more of the displays. The other information displayed might include, but is not limited to, which view is active (in the case of toggled views), status of built-in surgical tools, or status of articulation (for endoscopes that include active articulation), status of sheath bend angle or shape (for flexible endoscopes), sensor readings, or vital signs (for endoscopes incorporating or in use with vital function monitoring devices).

Each of the multiple views may incorporate stereoscopic, monocular, or biocular viewing means. Monocular viewing presents a two-dimensional image to one eye through one ocular. Biocular viewing presents the same image to each eye, using two oculars, though this is still a two-dimensional image. Stereoscopic images are created by presenting each eye with a slightly offset view of the scene (call them "left" and "right" views). If the system is properly designed and fabricated, the human brain will "fuse" the left and right views. This simulates human vision, and produces enhanced depth perception. In an endoscope, stereoscopic images are produced by fabricating two optical channels inside the instrument. In a direct-view stereoscopic endoscope, these images are viewed by looking directly through dual oculars with the eyes (biocular vision). In an electronic stereoscopic endoscope, the two optical views are focused onto one or more electronic sensors and viewed via a stereoscopic or volumetric electronic display. A multiple view endoscope of the present invention provides distinct multiple views of one or more objects, and each view may or may not be stereoscopic. It is important to note that the "multiple views" of the present invention are not the same as the "slightly offset views" used by stereoscopic imaging systems. The viewing angles in the present invention are independent of each other, unlike those of stereoscopic imaging systems. The distinct views of the present invention are not intended to fuse.

The endoscope may be completely reusable, completely disposable, or be partly reusable and partly disposable. The disposable portion of the endoscope may contain all, part, or none of the optical elements. The disposable portion may contain all, part, or none of the built-in surgical tools. The disposable portion may or may not include the sensor or ocular.

The endoscope may incorporate built-in surgical tools. These tools may include, but are not limited to stapling mechanisms, drug delivery devices, suturing devices, cutting tools, laser delivery systems, cauterizing systems, spectroscopic instruments, irrigation systems, photoinitiation systems, photocuring systems, photodynamic therapy instruments, suction tools, sensors, electronic devices, and heating or cooling systems.

Alternatively, the endoscope may provide access for such tools by way of one or more working channels. In this case, the tools are not built into the endoscope, but are separate instruments that are guided to the surgical site by insertion into and through an unobstructed passageway within the endoscope.

The endoscope is provided with one or more illumination channels to provide the light necessary for imaging. Each view may have its own illumination source, or one illumination channel may provide adequate illumination for multiple views. Illumination channels include elements such as glass, plastic, or hollow optical fibers or optical waveguides. These are connected to an external light source via a liquid-filled or fiberoptic cable. These may employ mechanical adapters, which may incorporate lenses, fiberoptic tapers or other means to couple light efficiently from the external source into the endoscope illumination system. The endoscope may also provide light to the surgical site via built-in light sources, such as LEDs (light emitting diodes). Other sources of light may also be incorporated, either internally to the endoscope or externally, including transillumination of the surgical site, whereby light originating externally or in an adjacent body space reaches the site by passing through tissue.

The endoscope may be encased in a rigid, semi-rigid (maleable), or flexible outer sheath. The sheath may be disposable, resposable (multi-use disposable), or reusable.

Flexible endoscopes may have a built-in means of active articulation. Articulation may be employed to view different areas of the surgical site, to help guide the endoscope through convoluted paths inside the body, or to guide and place instruments during a surgical procedure. Articulation is controlled by the physician manipulating levers or other controls at the proximal end of the endoscope, or it may be controlled robotically or by other means.

All the above and other characteristics and advantages of the invention will be further understood through the following illustrative and non-limitative description of preferred embodiments thereof, with reference to the appended drawings.

DETAILED DESCRIPTION OF THE INVENTION

Figure 1:
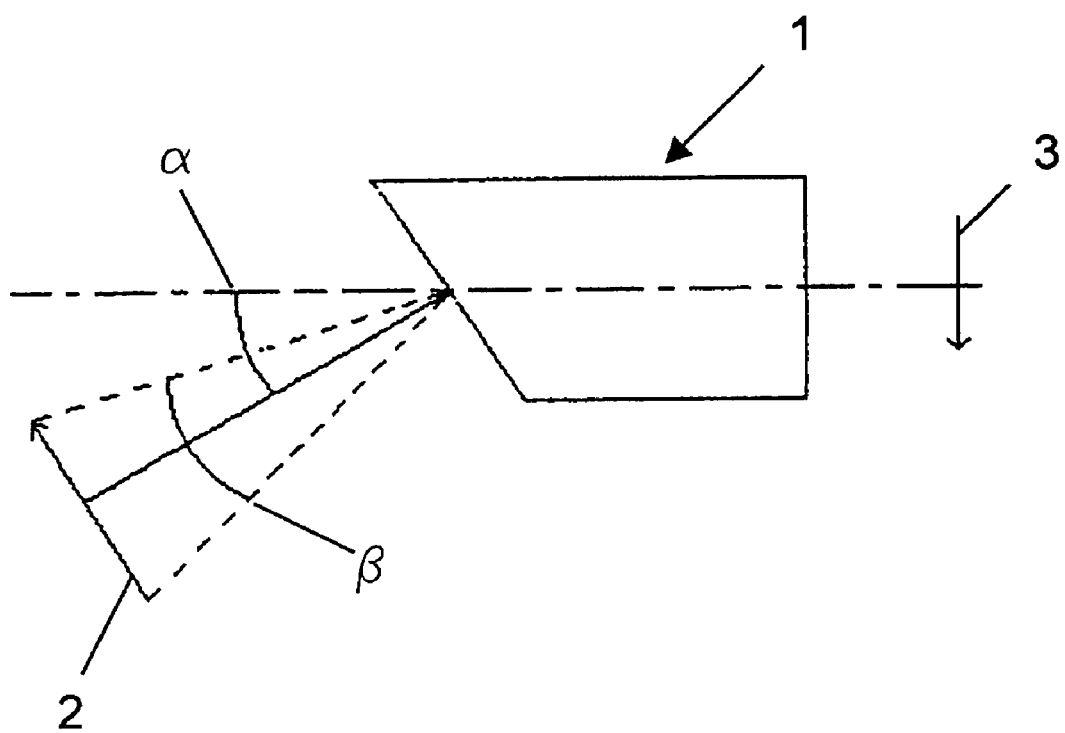
FIG. 1 schematically shows a typical endoscope objective.

Each of the multiple views of the invention is formed by an objective lens. FIG. 1 shows the configuration of a typical endoscope objective (1) and illustrates some of its properties. The angle between the mechanical axis of the distal tip of the endoscope and the optical axis as it enters the endoscope objective ($\alpha$) is the "angle of view". This angle of view refers only to the relationship between the optical and mechanical axes at the distal tip and does not take into account the variable direction of view provided by articulating (FIG. 7) the distal tip of the endoscope. Typical values for angle of view may range between 0 and 120 degrees. Non-zero angles of view are usually achieved by the use of prisms or mirrors in the objective optics. The field of view ($\beta$) of the endoscope objective describes the angular extent in object space that the lens can image. Field of view can be very narrow, approaching zero degrees, or may range up to 180 degrees. For example, a telescope will have a very small field of view with high magnification, while wide angle lenses (also know as "fish-eye" lenses due to the curved appearance of the image) have large fields of view with low magnification. The larger the field of view, the smaller the details will appear in the image. The image (3) of the object (2) can be located at or behind the last surface of the objective lens.

Figure 2A:
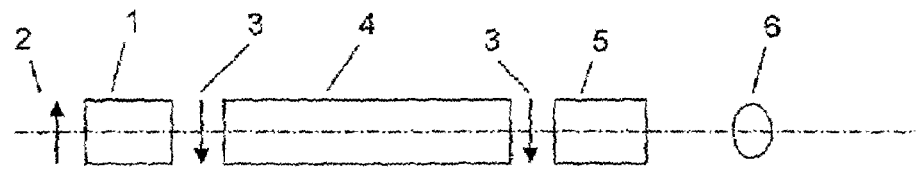
FIG. 2A through FIG. 2E schematically show endoscope configurations with a single optical channel.
Figure 2B:
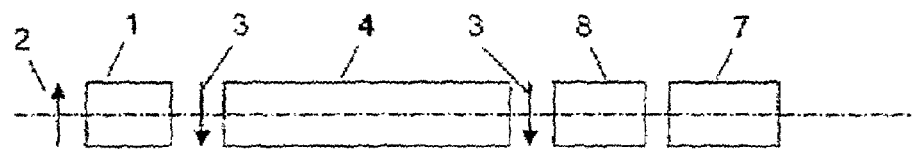
Figure 2C:
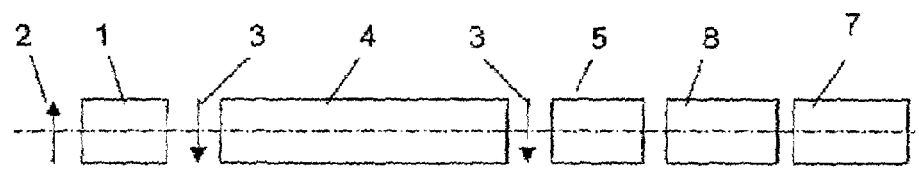
Figure 2D:
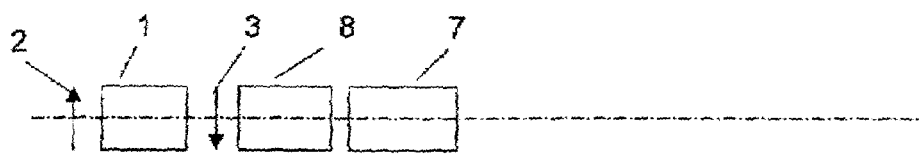
Figure 2E:
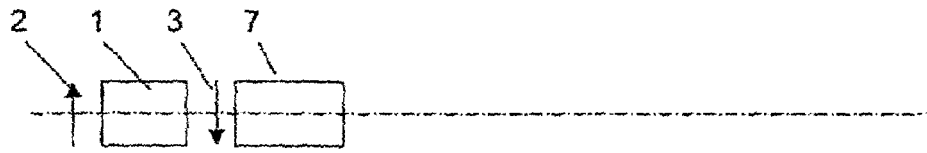

Looking at FIG. 2A through FIG. 2E, the image (3) formed by the objective lens (1) must be transmitted to a detector for viewing at the proximal end of the endoscope. An ocular (5) may be employed for direct viewing by the human eye (6), or the image may be formed on an opto-electronic sensor (7) (such as a CCD or CMOS sensor) that transforms the optical image into electronic signals. The electronic signals are then sent to a display, such as a video monitor, flat panel display, head-mounted display or liquid crystal display; where the image can be viewed by one or more people. FIGS. 2A to 2E show several configurations for each individual viewing channel of the present invention. FIG. 2A shows an objective lens (1) coupled to an ocular (5) by a relay optical system (4). A relay is an optical subsystem of the endoscope that transmits an image from the objective image plane to another location. Since an endoscope is usually much longer than the distance from the first surface of the objective to the objective image plane, relays are used to bring the image up to the proximal end of the endoscope, where it can be accessed by the viewing optics. Relays may consist of lenses or other optical imaging elements, or alternately a coherent (ordered) fiber optic image guide may be employed to transmit the image. Fiber optic image guides are usually used for flexible or semi-flexible endoscopes, while rigid endoscopes typically include a relay made up of a series of glass rods and lenses. FIG. 2B shows an objective lens (1) and relay (4) used in conjunction with an image sensor (7) connected optically via a coupling lens (8). The coupling lens images the relay's proximal image plane onto the surface of the sensor, where it is converted to an electronic signal and sent to the display for viewing. FIG. 2C shows an option in which an endoscope configured as shown in FIG. 1 is coupled to an image sensor (7) by a coupling lens (8) that clips or attaches onto the ocular (5) mount. FIG. 2D shows a configuration where the relay system is not used, and the image (3) is coupled directly from the objective image plane to the sensor surface (7) by a coupling lens (8). FIG. 2E is a similar option wherein the sensor surface may be placed directly in the objective image plane. This type of endoscope is sometimes referred to as a "chip-on-a-stick", and the sensor is imbedded in the distal end of the shaft instead of being located externally or at the proximal end.

Figure 3A:
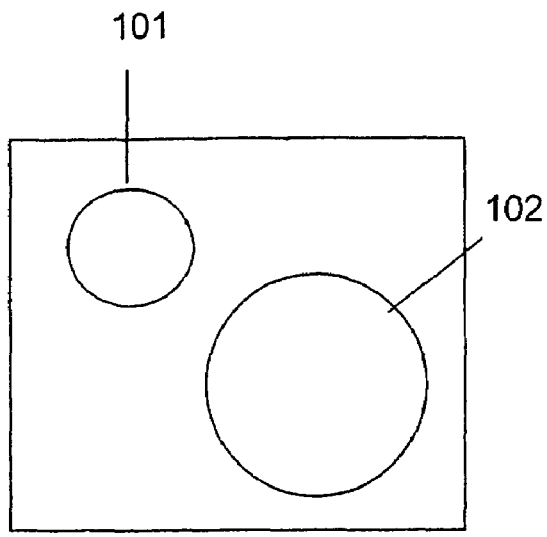
FIG. 3A through FIG. 3C show different options for displaying the multiple views.
Figure 3B:
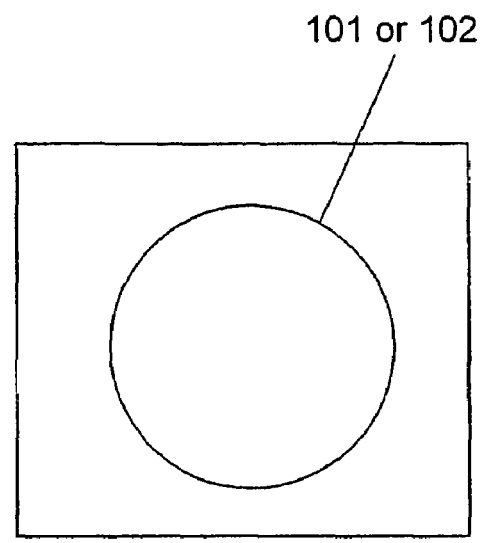
Figure 3C:
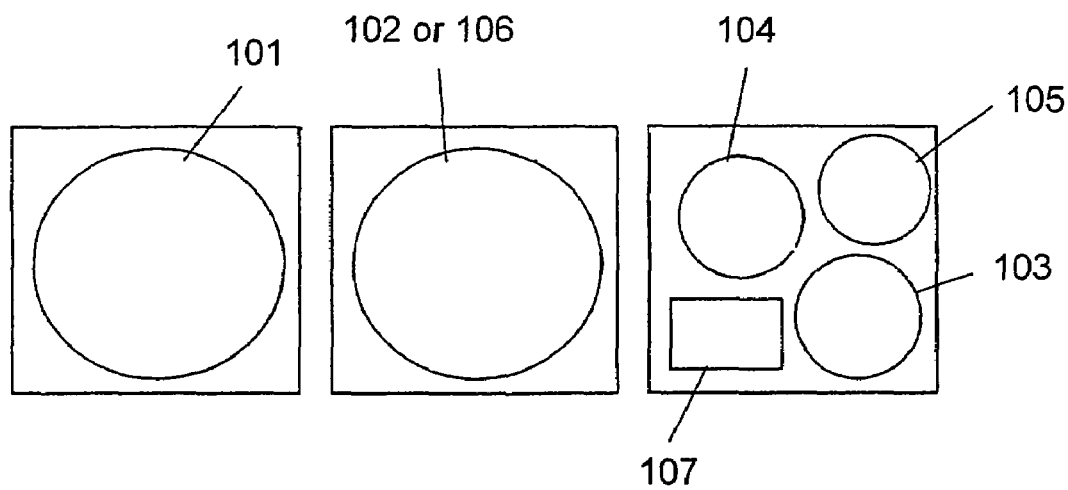

If an image sensor is utilized, there are many options for displaying the multiple views provided by the invention. Single or multiple displays may be used, with single or multiple views on each display. Options include, but are not limited to those shown in FIGS. 3. In each scenario, the display may also convey other information such as status of built-in surgical tools, status of the articulation, or readouts from vital signs monitors for example. FIG. 3A illustrates having multiple views (1) and (2) arranged on a single display. The views may take on any shape and do not need to be of equal size. FIG. 3B shows multiple views (101) or (102) that are accessed on a single display by toggling between the views as needed. In another preferred embodiment of the present invention, a multiplicity of displays may provide visual access to a multiplicity of views. Each display may contain one or more views that can be accessed simultaneously, singly, or by toggling between views. Zero or more of the displays may also show status indicators or other information. As shown in FIG. 3C, one display is showing view (101) individually, a second display is toggling between views (102) and (106), and the third is presenting views (103), (104), and (105), simultaneously with status indicators (107).

Figure 4A:
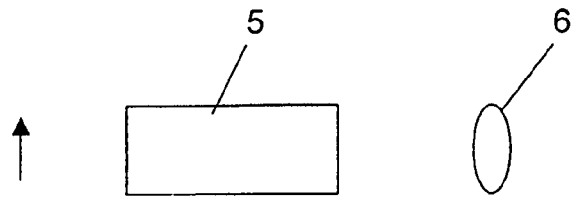
FIG. 4A schematically shows the ocular types for monocular viewing.
Figure 4B:
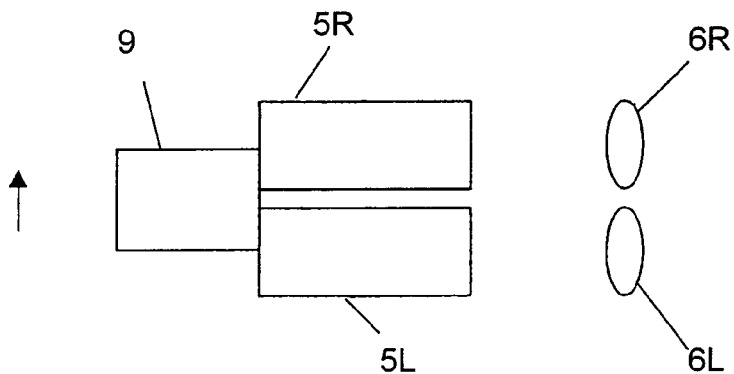
FIG. 4B schematically shows the ocular types for biocular viewing.
Figure 4C:
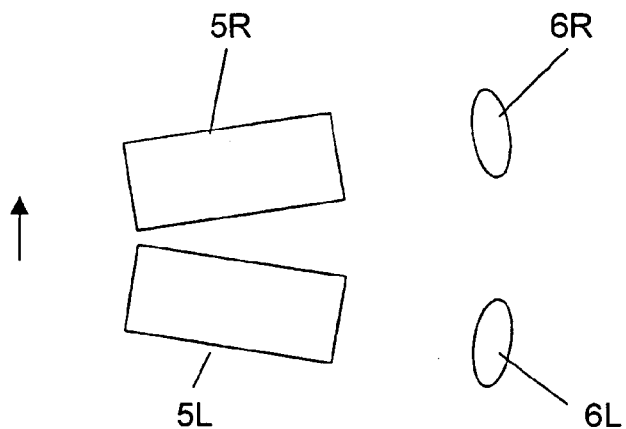
FIG. 4C schematically shows the ocular types for stereoscopic viewing.

FIG. 4 show different ocular types for monocular, binocular, and stereoscopic viewing. It is important to note that while stereoscopic viewing may be provided for one or more of the multiple views, the optics used to provide a stereoscopic view do not present "multiple views" as defined with reference to the present invention. Key differences are that stereoscopic optical channels provide slightly offset images of the same object area; while in the present invention the optical channels that provide multiple views have substantial linear or angular offsets, or both, and do not provide images of the same object area. FIG. 4A illustrates the schematic for monocular viewing, which is typical of most endoscopes that include an ocular. One ocular (5) provides access to the image for a single eye (6), which can be either the left or the right eye. Biocular optics use splitting optics (9) to provide the same exact image to both eyes via two oculars, one for each eye as shown in FIG. 4B. Here the addition of the letters "L" and "R" designate left and right for both the oculars (5) and the eyes (6). The stereoscopic ocular arrangement shown in FIG. 4C provides a slightly offset view of the image to each eye (6L and 6R) via two oculars (5L and 5R) that are offset. This simulates normal human vision where each eye captures a slightly offset view and allows for some depth perception.

Figure 5A:
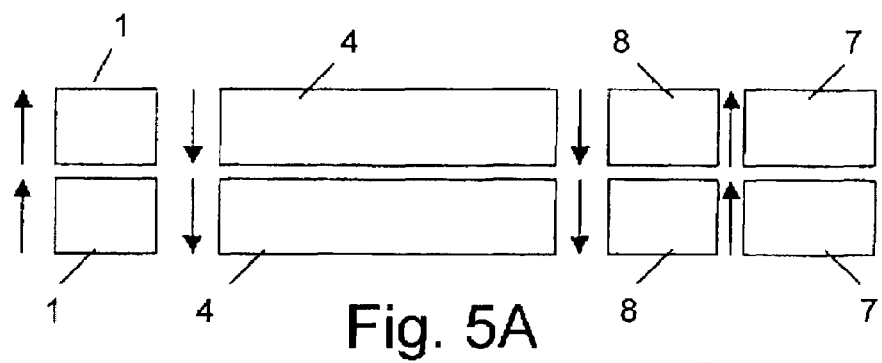
FIG. 5A through FIG. 5D schematically show different configurations for the dual optical channels for dual views.
Figure 5B:
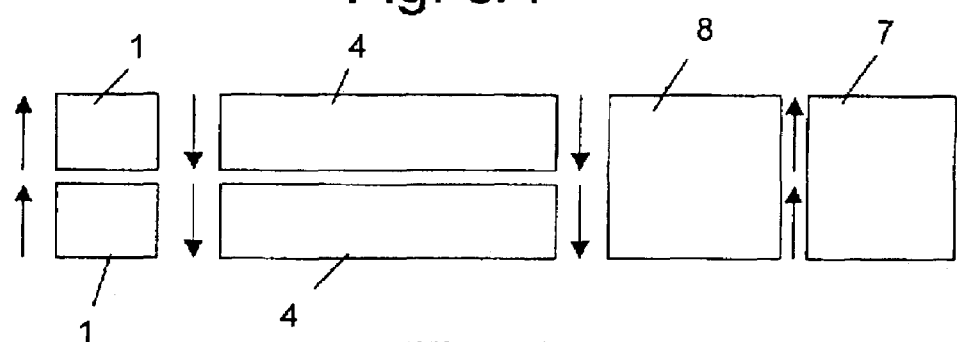
Figure 5C:
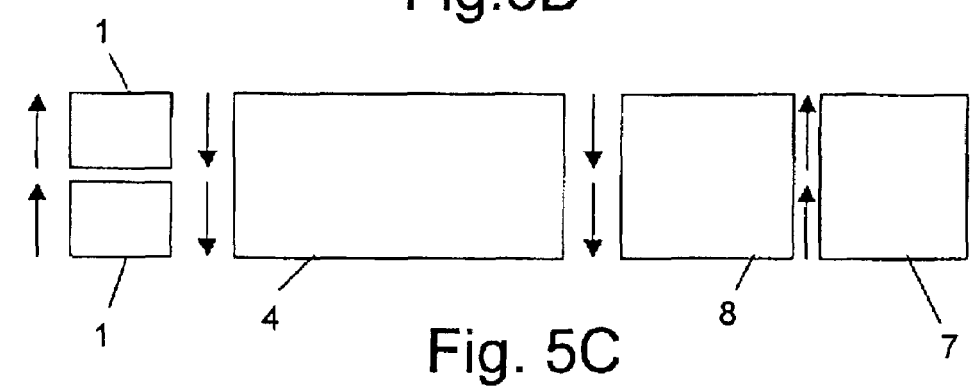
Figure 5D:
Figure 5D:
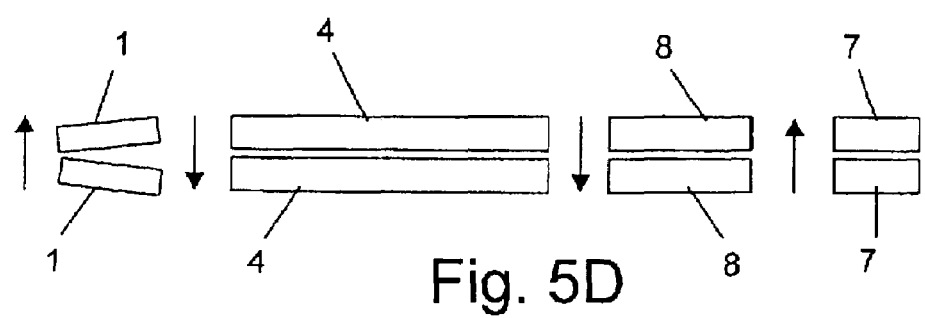

According to a preferred embodiment of the present invention, each of the multiple views is formed by a unique objective lens (or pair of objective lenses for stereoscopic viewing). This means that at the distal end, there will be one optical channel per view (or two for stereoscopic viewing). These separate optical channels may continue through the entire endoscope as shown in FIG. 5A. This figure shows an endoscope having two views. Each view is carried to a separate image sensor (7) by its own unique optical channel. Since there are two views, there are two relays (4), two coupling lenses (8), and two sensors (7). In FIG. 5B, a alternative is shown where the endoscope has two views, that have unique objectives (1) and relay optical channels (4), and a single coupling lens (8) and image sensor (7) captures both views. The coupling lens and sensor may image the views together, or one at a time by switching between them actively or passively. A third alternative, shown in FIG. 5C, has two unique objectives (1) that capture two views, with a single relay system (4), coupling lens (8), and sensor (7) providing access to the views. As in the system shown in FIG. 5B, the access may be simultaneous or one at a time. FIG. 5D illustrates an endoscope having two views, one of which provides stereoscopic imaging. The upper (non-stereo) view is carried by a single optical channel. The lower (stereo) view contains a set of two optical channels that are slightly offset at the distal end. The two optical channels present images of the object that originate from slightly different locations. This simulates normal human vision in which each eye views a scene from its own unique location and the brain integrates the differences in the image on each eye to formulate depth cues.

Figure 6:
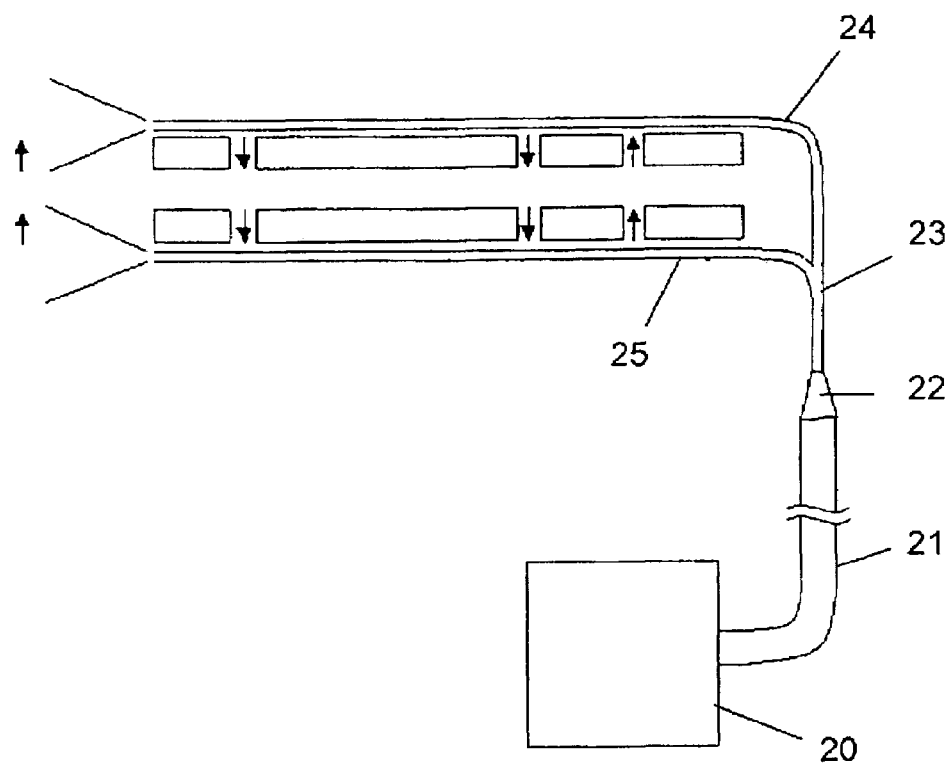
FIG. 6 schematically shows a typical endoscope illumination system.

According to another preferred embodiment of the present invention, the endoscope provides illumination to the views via single or multiple illumination channels. FIG. 6 shows one such configuration where an endoscope with two views (as illustrated in FIG. 5A) has a separate illumination channel for each view. Light from an external source (20) is transmitted to the endoscope via liquid-filled or fiberoptic cable (21). Coupling optics (22) at the interface insure that the light is efficiently coupled into the internal illumination fibers (23). The illumination fibers are split into two channels (24 and 25) internally within the endoscope to provide light to each view individually.

Figure 7:
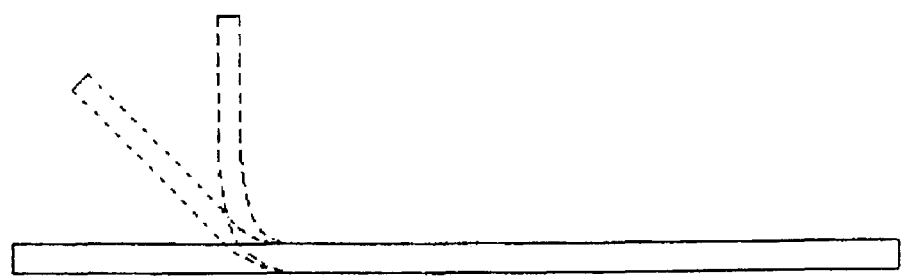
FIG. 7 schematically shows an endoscope sheath with articulation.

The present invention utilizes a rigid, a semi-flexible, or a flexible sheath. If the endoscope is flexible, it may also be capable of articulation in one or more axes. FIG. 7 shows an example of 90-degree articulation in one axis on a flexible sheath.

As an illustrative, but not limitative, example of the invention, an endoscope with dual optical channels which permits carrying out a new surgical treatment for GastroEsophageal Reflux Disease (GERD) is now described.

The new procedure is an alternative to current treatment options and has been described in the above referenced international patent application (PCT/IL01/00238). This procedure is carried out using a surgical endoscopic device provided with at least one flexible portion, which is, in a preferred embodiment, an articulation section and a stapling device comprising a staple-firing portion and an anvil portion. According to preferred embodiments of the invention, the staple firing portion (sometimes called the cartridge) is located proximately to the proximal end of the articulation section and the anvil portion is located on the distal end or tip of the articulation section.

According to the preferred embodiment of the invention, the endoscope employs a two-way articulation system. In this case, completely bending the articulation section using a fixed radius of curvature brings the two portions of the stapler into alignment. Further, the parts of the stapling device are in correct working relationship when two alignment/locking pins that are stored in the anvil portion are extended and engage and lock into receptacles on the staple firing portion.

The staple firing portion contains a staple cartridge containing one or a plurality of arrays of staples. Each array consists of one or a plurality of staples. The arrays of staples are fired by staple pushers actuated by cams actuable by proximal means. The staple cartridge is indexable after the firing of each of the arrays of staples by the action of a proximal actuating device.

The endoscopic device for the GERD procedure should preferably comprise viewing means, typically a video camera. In a preferred embodiment of the invention, two separate optical channels are provided to provide two independent images, one from the area of the anvil at the distal tip and one from the area of the staple cartridge in the shaft of the endoscope. As will be apparent to the skilled person, it is usually necessary to provide illumination apparatus for viewing purposes. Additionally, other conventional endoscopic devices and accessories, such as water and/or air supply and/or suction, and/or ultrasound are provided.

Based on the above, an illustrative preferred embodiment of the present invention may, therefore, consist of the following elements:

Multiple optical channels;
   An optical channel at the distal tip to visualize insertion and stapling from the distal end (which also contains the stapler anvil);

A second optical channel located at the stapling backstop on the endoscope side wall to visualize staple penetration inside the esophagus from the "stapler side";

A stapler module located intermediately along the endoscope shaft that may contain components of the optic system. This module is preferably disposable, but may be resposable or reusable;

A stapler anvil module at the distal tip that may contain components of the optic system. This module is preferably disposable, but may be resposable or reusable;

A robust, one-way articulating section e.g. capable of up to about 270° articulation to distend the fundus of the stomach and position the stapler; and A single display showing both views simultaneously, with optional status indicators for the endoscope articulation, stapling operation, or both.

Figure 8A:
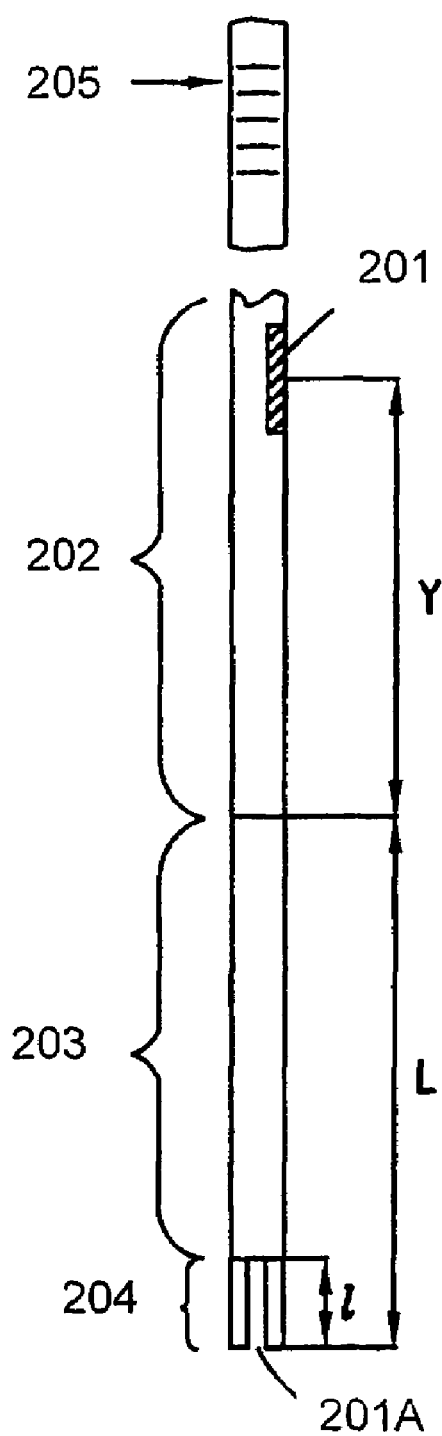
FIG. 8A schematically illustrates the fixed portion and the bending distal portion of the device of the invention.

Looking now at FIG. 8A, the distal portion of the device of the invention is schematically shown. This portion comprises a fixed, non-bending section, indicated at 202 (wherein is located the stapler ejector and the objective optics of the "stapler view" optical channel), and an articulating section 203, and the distal end 204 of length "$\ell$".

Articulating section 203 is similar in design to that of conventional endoscopes, but possesses several unique features. In order to simplify the alignment procedure and at the same time achieve maximum accuracy, a one-way articulation design has been chosen. This means that the articulating section is constrained to move in one direction only (i.e. the tip of the endoscope can only move from straight ahead to one side). Secondly, the device must be able to bend further than conventional endoscopes in order to carry out the required medical procedure. Finally the articulating section must be strong enough to provide a significant force against the tissues during fundus distension and stapling.

The fixed section 202, contains the stapler cartridge. The stapler ejector has a side shooting design and requires an anvil, which is located on the end of the distal tip. Both the stapler cartridge and the anvil module are replaceable and fit into pockets on the shaft and distal tip. These pockets are labeled 201 and 201A respectively in FIG. 8A. The stapling elements at 201 and 201A, together, form the entire stapling assembly.

Articulation of the device is carried out in a conventional manner. Since the mechanism and operation of articulation activation are well known to the man of the art, they will not be discussed here for the sake of brevity.

Figure 8B:
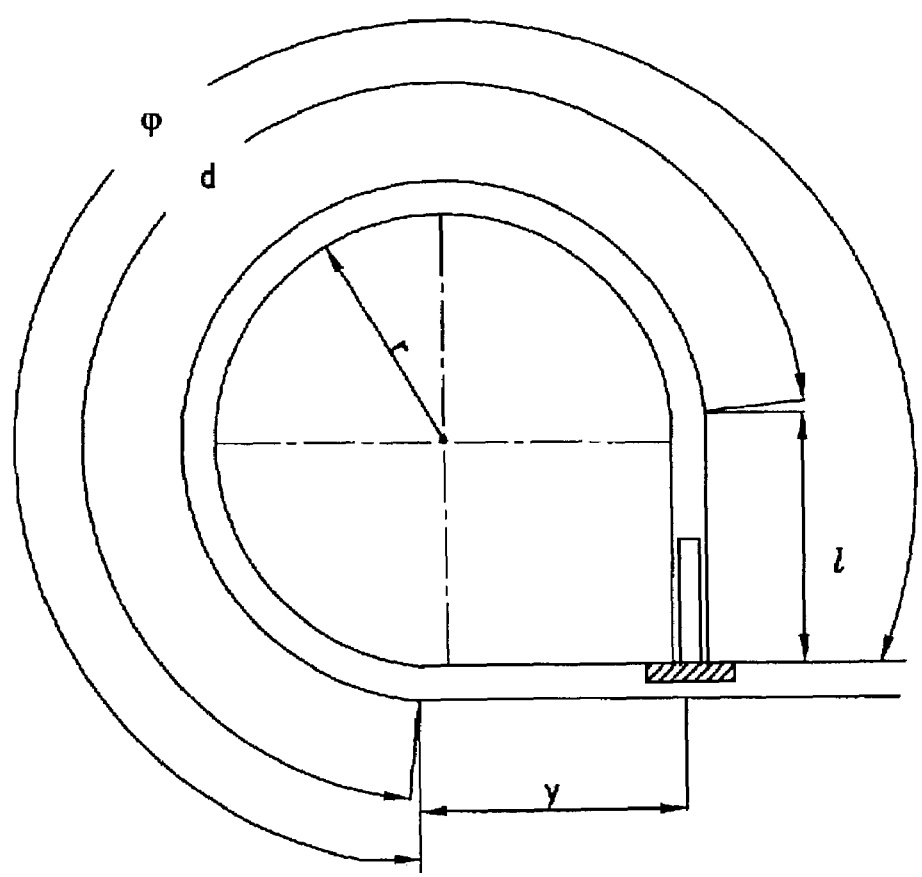
FIG. 8B schematically illustrates the bending of the endoscope of FIG. 5A through its fixed bending angle.

FIG. 8B shows the device of FIG. 8A in a fully bent position. The articulation section 203 has been bent through bending angle φ using fixed radius of curvature r. The values of radius r and the length L (FIG. 8A) are determined by the fixed values $\ell$(length of the rigid distal tip) and y (the distance from the stapler cartridge to the junction of the fixed and bending portions of the distal end of the endoscope) in such a way that bending the device completely brings the two parts of the stapler assembly exactly into alignment.

Exact alignment is accomplished by deploying the locking pins to hold the endoscope in the position shown in FIG. 8B during the surgical procedure. In a preferred embodiment of the invention, locking pins are stored in the anvil section of the stapler. By using an activator 1 shown at 302 in FIG. 10), the physician can deploy the pins through the tissue of the fundus and esophagus walls and engage sockets in the staple ejector module. The method of deploying the locking pins is well known to the man of the art and will therefore not be discussed here for the sake of brevity.

Positioning markings 204 maybe located on the device (as indicated in FIG. 8A), at the extremity outside the patient, to provide information on the length of device that has been introduced into the patient.

Figure 9A:
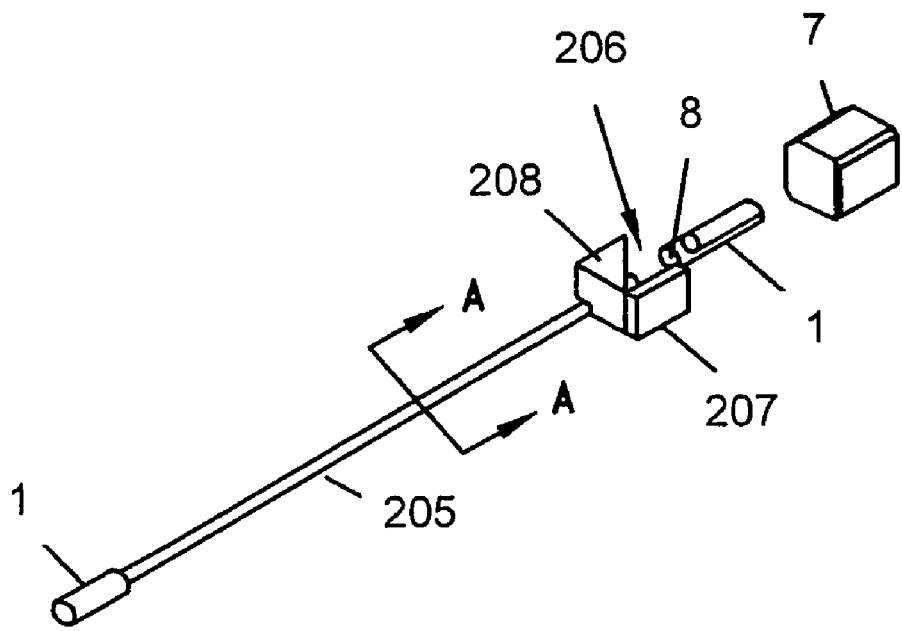
FIG. 9A is a schematic view of an optical assembly showing dual optical channels.

In order to see both sides of the staple as it is placed, and to assure proper joining of both fundus and esophageal tissues, a preferred embodiment of the invention employs the use of two optic channels (FIG. 9A). In this embodiment, an objective lens 1 captures the image from the tip of the scope (the "distal view"). A flexible fiberoptic image guide 205 carries the image about 12 cm proximally where it is focused by a coupling lens 8 onto a CCD sensor 7. This view fills the main part of the video monitor (401 in FIG. 11), and is always displayed, since it is used during insertion, distention, and stapling. A "stapler view" (402 in FIG. 11) is simultaneously projected onto one corner of the CCD and thus appears in one corner of the monitor. This is a view from the endoscope shaft, looking sideways from the vicinity of the stapler, which is located at position 206 in FIG. 9A. The optical path of this image starts with an object perpendicular to the axis of the endoscope. The optical path travels through the stapler backstop 207 and clear portions of the stapler module and with the aid of right angle prism 208 and objective lens 1 an image is produced on the CCD 7. This view may only be activated during the stapling process. After stapling, the distal view shows the closed staple(s) from the stomach side, and the stapler view shows the staple(s) from the esophageal side. These multiple views provide confidence that each staple is properly placed before repositioning the instrument for the next shot.

Exact alignment is accomplished by deploying the locking pins to hold the endoscope in the position shown in FIG. 8B during the surgical procedure. In a preferred embodiment of the invention, locking pins are stored in the anvil section of the stapler. By using an activator (shown at 1 in FIG. 10), the physician can deploy the pins through the tissue of the fundus and esophagus walls and engage sockets in the staple ejector module. The method of deploying the locking pins is well known to the man of the art and will therefore not be discussed here for the sake of brevity.

Positioning markings 4 may be located on the device (as indicated in FIG. 8A), at the extremity outside the patient, to provide information on the length of device that has been introduced into the patient.

In order to see both sides of the staple as it is placed, and to assure proper joining of both fundus and esophageal tissues, a preferred embodiment of the invention employs the use of two optic channels (FIG. 9A). In this embodiment, an objective lens 1 captures the image from the tip of the scope (the "distal view"). A flexible fiberoptic image guide 2 carries the image about 12 cm proximally where it is focused by a coupling lens 6 onto a CCD sensor 8. This view fills the main part of the video monitor (1 in FIG. 11), and is always displayed, since it is used during insertion, distention, and stapling. A "stapler view" (2 in FIG. 11) is simultaneously projected onto one corner of the CCD and thus appears in one corner of the monitor. This is a view from the endoscope shaft, looking sideways from the vicinity of the stapler, which is located at position 5 in FIG. 9A. The optical path of this image starts with an object perpendicular to the axis of the endoscope. The optical path travels through the stapler backstop 3 and clear portions of the stapler module and with the aid of right angle prism 4 and objective lens 7 an image is produced on the CCD 8. This view may only be activated during the stapling process. After stapling, the distal view shows the closed staple(s) from the stomach side, and the stapler view shows the staple(s) from the esophageal side. These multiple views provide confidence that each staple is properly placed before repositioning the instrument for the next shot.

The display may have the option of switching the second view off when it is not needed by controlling illumination to each view. The first view will typically be active continuously but also may be switched off.

Figure 9B:
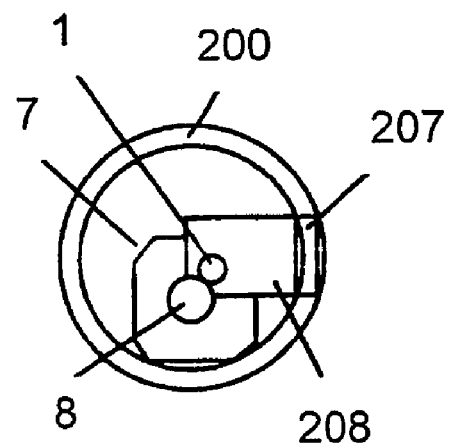
FIG. 9B is a cross-sectional view of the assembly of FIG. 8A looking from the distal end.

FIG. 9B is a cross-sectional view of the optical system of FIG. 9A taken at A—A, looking toward the proximal end of the endoscope, showing how the various optical elements are arranged within the sheath of the endoscope 200.

Figure 9C:
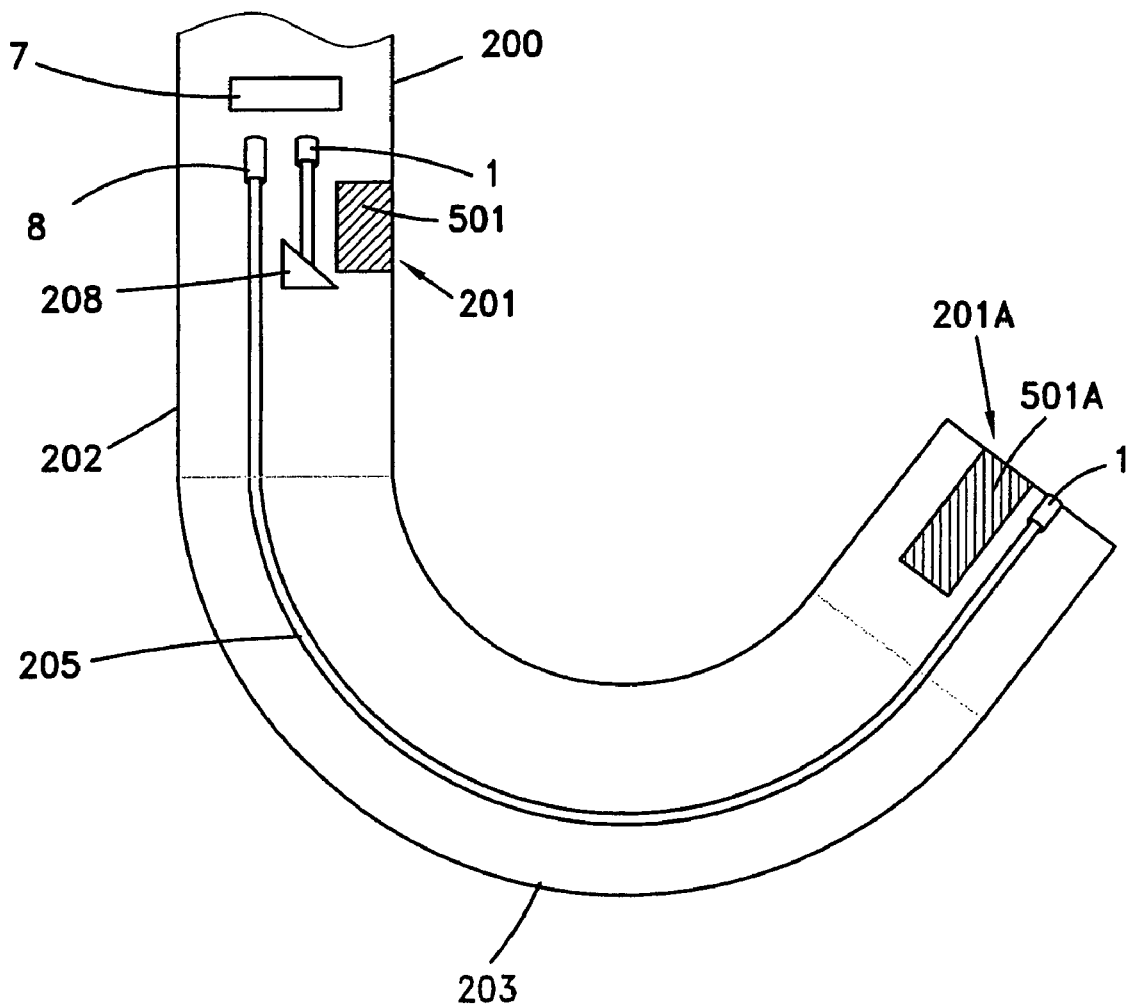
FIG. 9C schematically shows an exemplary embodiment of the apparatus in accordance with the present invention.

FIG. 9C shows a preferred embodiment of the invention in which endoscope 200 comprises an anvil portion 501A of a stapling device located in pocket 201A, next to the objective lens 1 of a first optical channel on its distal tip. Endoscope 200 further comprises articulation section 203 and non-bending section 202, in which is located the staple-firing portion 501 of the stapling device in pocket 201 next to an objective lens 1 of a second optical channel.

Figure 10:
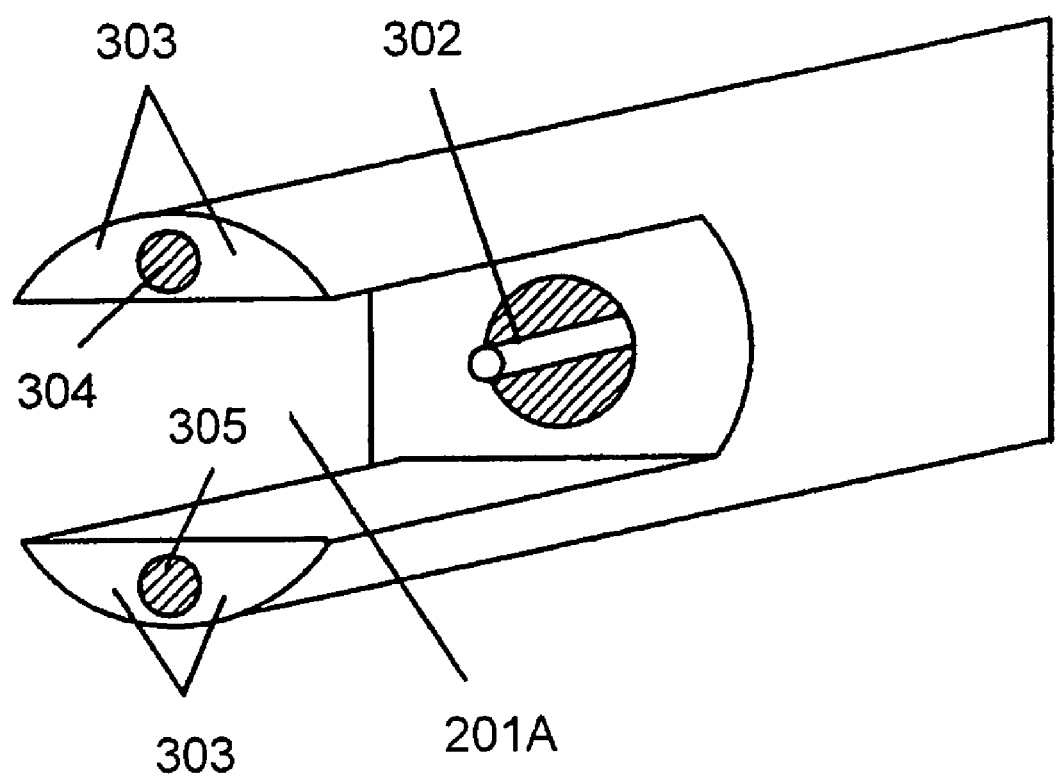
FIG. 10 is a detailed view of the distal tip of the endoscope.

FIG. 10 shows the distal tip of the endoscope. The anvil module of the stapler assembly goes into the socket 201A. An actuator for locking pins that are contained in the anvil is shown at 302. A channel for suction or irrigation is shown at 305. The image channel is 304 and 303 represents illumination fibers.

The built-in surgical tools of the preferred embodiment of the invention consist of stapler and anvil modules and suction capability. A staple remover may also be incorporated. The stapler modules may be disposable or resposable items. The disposable portions of the endoscope may also contain parts of the optical channels, the outer sheath, a "bite block" for insertion of the scope orally, or other parts of the endoscope. The stapling module may place a single staple or a pattern of staples with each shot. The stapler contains one or more arrays of multiple staples that are advanced automatically after each shot.

Figure 11:
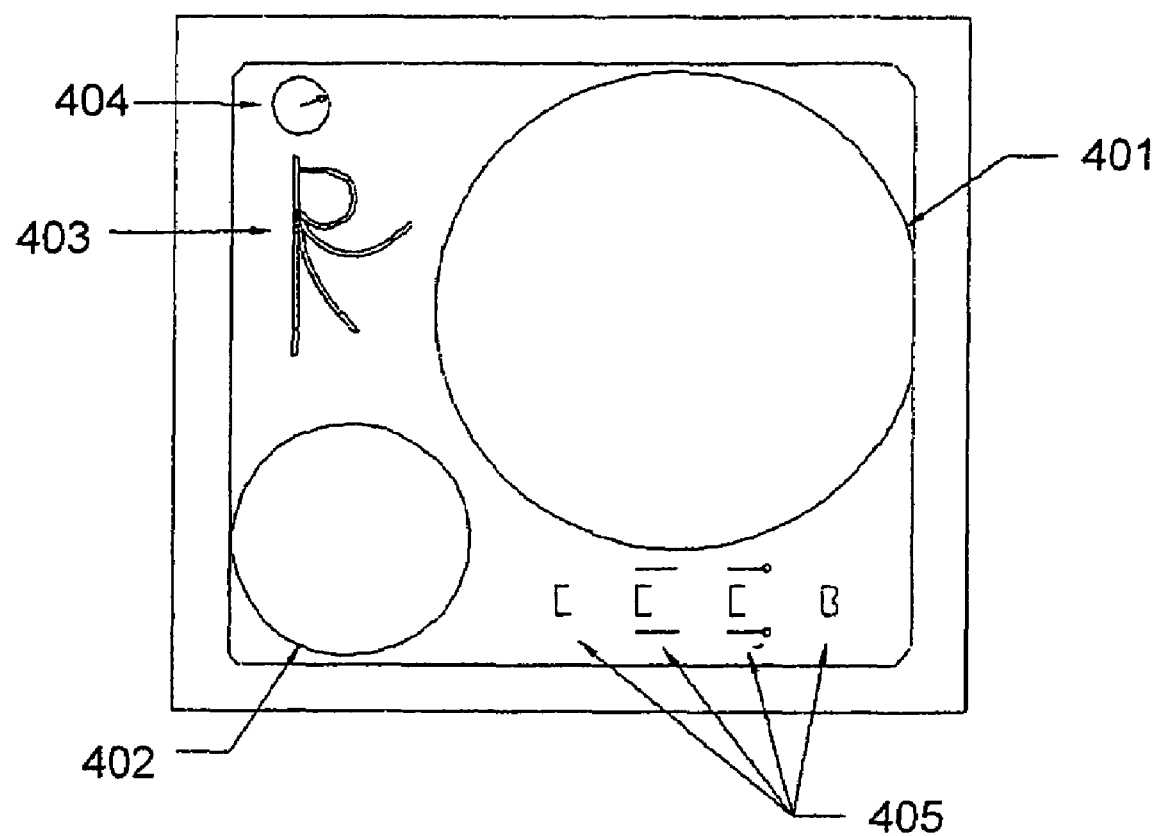
FIG. 11 shows a display layout for a preferred embodiment of the invention.

The display may incorporate status indicators relating to the various functions of the endoscope. For example in FIG. 11, 403 shows the status of the articulation of the distal end, 4 404 shows the rotation of the endoscope around the long axis, and 405 shows the stapler status.

The partial fundoplication of the fundus of the stomach of a patient may be carried out with the endoscope of the invention by:
  a) moving the distal tip of the endoscopic device so as to engage the fundus of the patient and to displace it toward the lower part of the esophagus;
  b) bringing said stapling assembly into working positioned relationship by moving the distal portion of said endoscope through a fixed bending angle;
  c) determining when said two separate elements of said stapling assembly are aligned by viewing them through the viewing means of said endoscope and by the deployment of locking pins provided on the distal tip of said endoscope;
  d) ejecting a plurality of staples from said staple-ejecting device, thereby to connect the tissue between them;
  e) releasing the locking pins and straightening the distal bending portion of said endoscope; and
  f) rotating the endoscopic device relative to the axis of the esophagus and repeating steps (a) through (e) for as many times as needed to achieve the desired partial fundoplication.

Figure 12A:
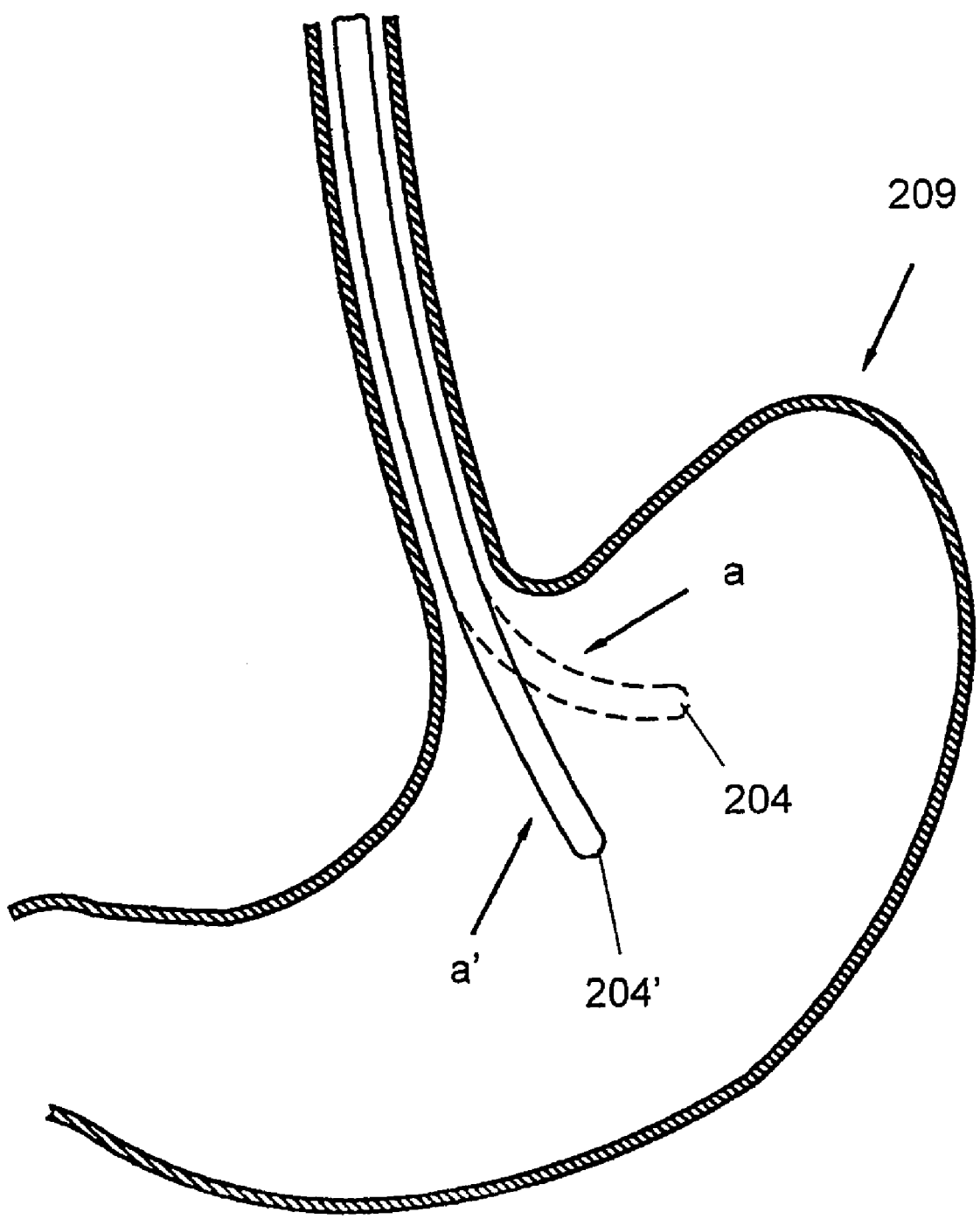
FIGS. 12A, 12B, and 12C schematically illustrate the mechanical procedure involved in the fundoplication using a device according to the invention.

The mechanical operation of the device involves the bending of the articulation section of the device so as to engage the fundus of the stomach with the distal tip, and to move it toward the lower esophagus. This is schematically illustrated in FIGS. 12(A, B, and C). In FIG. 12A, two positions of the device are shown, a and a'. Position a' is the initial position after the device has been inserted through the mouth and esophagus of the patient to the desired position. Position a illustrates the beginning of bending of articulation section of the device, towards the fundus 209, the tip being indicated as 204.

Figure 12B:
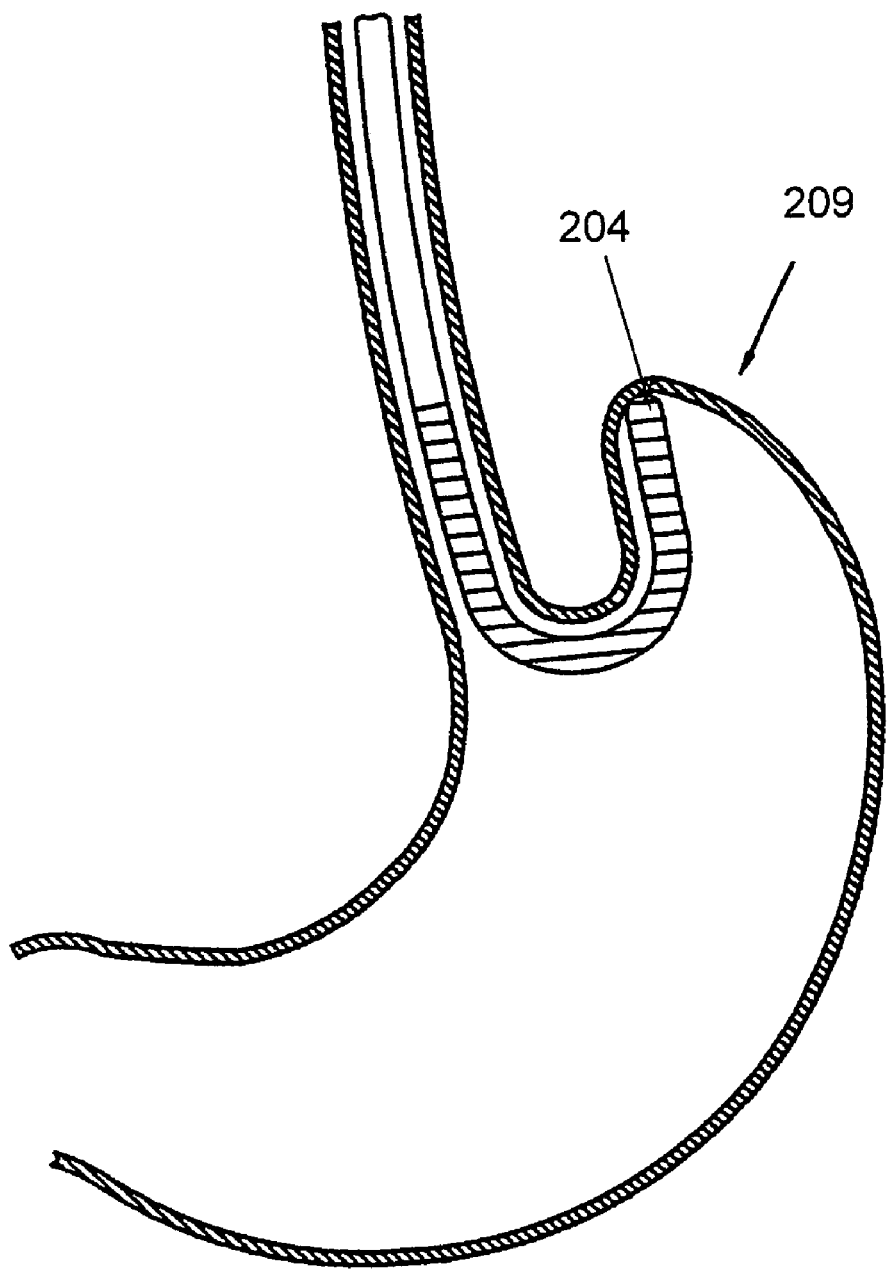

In FIG. 12B, the bending of the device has proceeded to the stage in which the distal tip 204 has encountered the wall of the fundus 209 and started to pull it towards the lower region of the esophagus.

Figure 12C:
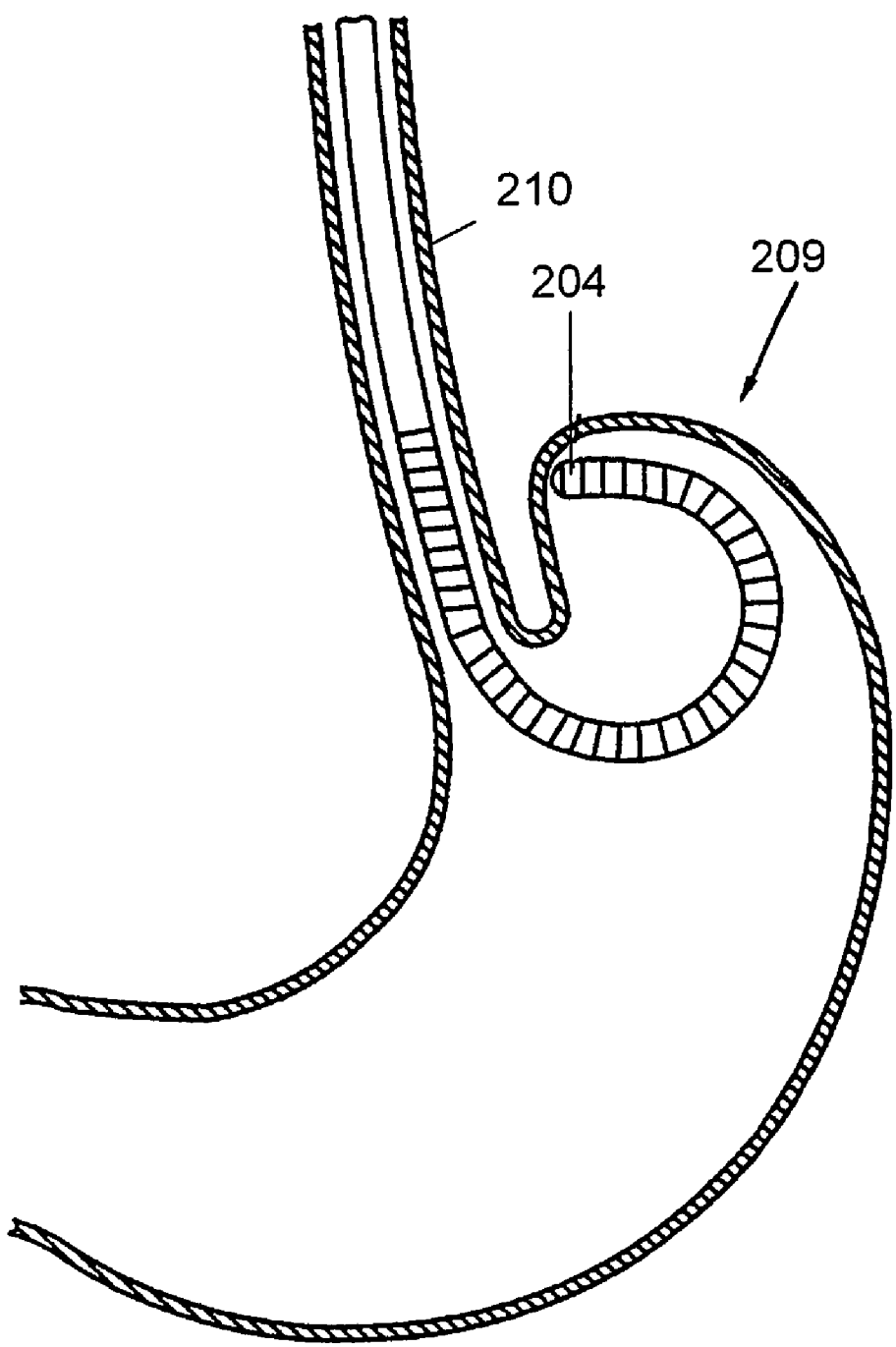

In FIG. 12C, the situation shown is that in which bending of the device has been completed, and the distal tip 204 has caused the fundus 209 to move from its original position to a position near the lower esophagus 210. In this position, the fundus is correctly positioned by tip 204 and it is possible to carry out the stapling together of the fundus and esophagus.

Figure 13:
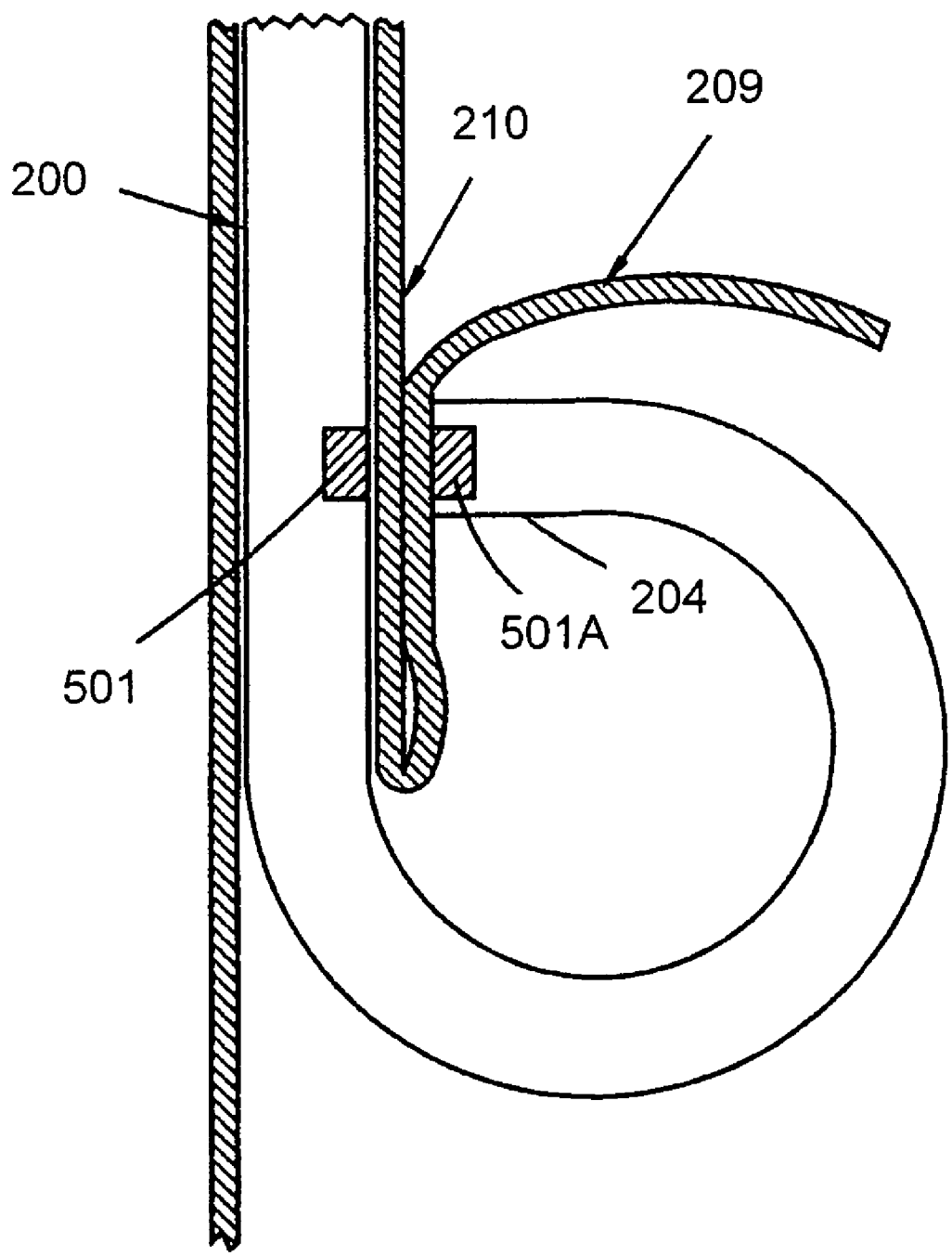
FIG. 13 schematically illustrates the positioning of the device prior to stapling.

FIG. 13 is a more detailed view of the situation depicted in FIG. 12C. Here is schematically shown the alignment between the staple cartridge 501, mounted on the endoscope shaft 200 within the esophagus 210, and the anvil 501A mounted on the distal end 204 within the fundus 209.

In order to fasten the lower part of the fundus 209 (FIG. 13) to the lower part of the esophagus 210, by means of the stapling assembly, it is imperative that element 501 and element 501A be brought into the correct working positioned relationship, so that the staples, when ejected, perform their required task. Failure to bring the parts of the stapling assembly into the correct positioned relationship may be fatal, as it will result in the staple not being correctly positioned or folded, and in a high risk of damaging the tissue where the stapling has been performed.

Figure 14A:
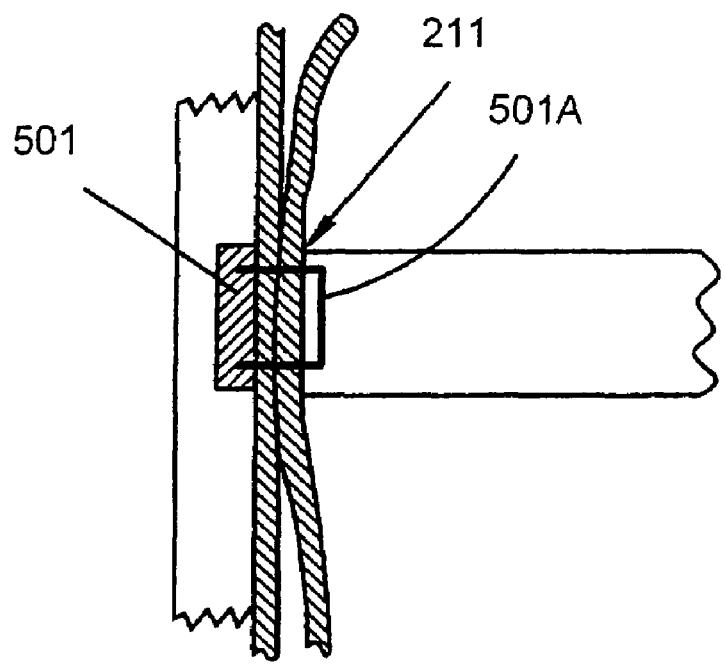
FIG. 14A schematically shows the locking needles deployed from the anvil module and locked into the staple ejector module.

As described above, the design of the device assures proper alignment. The surgeon is able to verify this alignment, as well as the proper distention of the fundus towards the esophagus, by using the visual means provided at the distal tip of the endoscope. Further, as the two parts of the stapler are pressed together, the tissue is pressed between them and it is possible to see through the tissue using the visual means provided on the cartridge side. Final alignment is accomplished by deploying the locking pins that are provided in the anvil section of the stapler. FIGS. 14 shows the relevant part of the device and tissue. In FIG. 14A, the locking pins (collectively indicated at 211), that were stored in the anvil assembly 501A, have been deployed through the tissue of the fundus and esophagus walls and have engaged the sockets in the stapler cartridge 501. The locking pins not only perform the final alignment, but also increase the clamping force during the stapling which is now carried out.

Figure 14B:
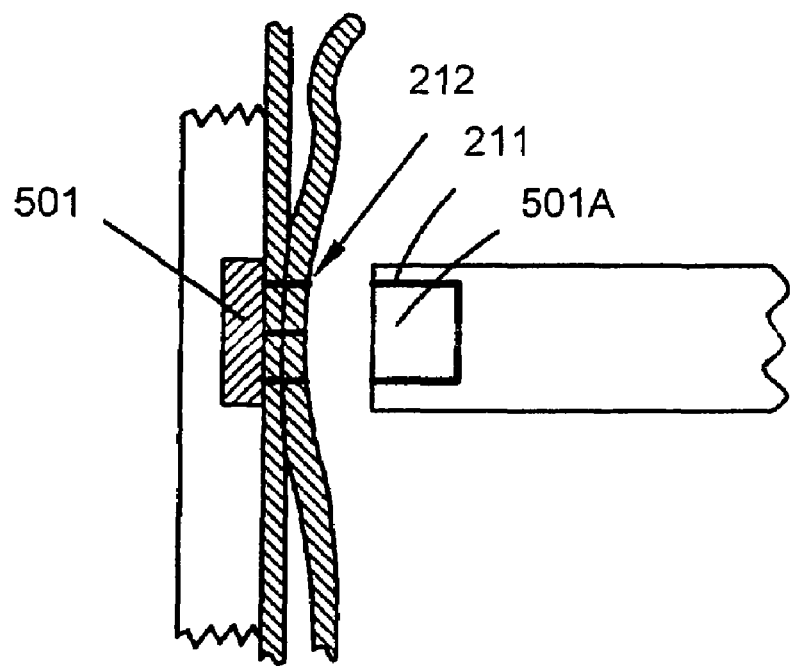
FIG. 14B schematically shows the situation after the staples have been fired and the locking needles withdrawn.

FIG. 14B shows the situation after the stapling has been effected. Staples, (collectively indicated at 212), have engaged between the fundus and the esophagus, at the specific location on which it was operated. After carefully inspecting the staples the surgeon has retracted the locking pins. The surgeon next straightens the endoscope, and moves the device by rotating it to its next location. When the next location is reached, the bending/aligning procedure is repeated, and the stapling is effected again.

While embodiments of the invention have been described by way of illustration, it will be understood that the invention can be carried out by persons skilled in the art with many modifications, variations and adaptations, without departing from its spirit or exceeding the scope of the claims.

What is claimed is:

1. An endoscope comprising: a single continuous shaft including, a sheath, an articulation section attached to a distal end of said sheath and, a distal tip attached to a distal end of said articulation section, and two or more separate optical channels that produce two or more distinct views, each of said optical channels comprising an objective lens, located at a distal end of said respective optical channel and a means of capturing and/or viewing the image; wherein the objective lens of the separate optical channel, which produces the first of said distinct views is located at a first location, said first location located on said distal tip, and the objective lens of the optical channel, which produces the second of said distinct views is located at a second location, said second location located either on a proximal end of said articulation section or on the sheath of said endoscope; wherein the distance between said first location and said second location, measured along the longitudinal axis of said endoscope, is fixed.

2. An endoscope according to claim 1, in which each of the distinct multiple views is selected from the group comprising: a monocular view, produced by a single optical channel; a binocular view, produced by two optical channels; and a stereoscopic view, produced by two optical channels.

3. An endoscope according to claim 1, in which the components of the optical channels and a display apparatus are chosen such that said endoscope can operate in either the visible, ultraviolet, infrared, or x-ray portions of the electromagnetic spectrum.

4. An endoscope according to claim 1, in which the objective lens has a focal length selected from the group comprising: fixed focal length, multiple focal lengths, or variable focal lengths.

5. An endoscope according to claim 1, in which each of the distinct views is at an angle of between 0 and 180 degrees with respect to the mechanical axis of said endoscope.

6. An endoscope according to claim 1, in which the field of view of each of the optical channels has an angular view of up to 180 degrees or more.

7. An endoscope according to claim 1, further comprising a stapling device, said stapling device comprising a staple-firing portion and an anvil portion, wherein one of said portions is located at the first location and the second of said portions is located at the second location.

8. An endoscope according to claim 1, wherein the means for capturing or viewing the image comprise one or more of the following elements:
 (a) an optical relay system;
 (b) an ocular; and
 (c) a coupling lens suitable to deliver the image acquired by the objective lens to an image sensor and display apparatus.

9. An endoscope according to claim 8, in which the ocular and the coupling lens have a focal length selected from the group comprising: fixed focal length, multiple focal lengths, or variable focal lengths.

10. An endoscope according to claim 8 comprising an image sensor and a display apparatus, wherein at least two of the two or more distinct views are displayed simultaneously on the display apparatus.

11. An endoscope according to claim 1, in which the field of view of the optical channels is circular.

12. An endoscope according to claim 1, in which the field of view of the optical channels is rectangular.

* * * * *

UNITED STATES PATENT AND TRADEMARK OFFICE
CERTIFICATE OF CORRECTION

PATENT NO. : 6,997,871 B2  
APPLICATION NO. : 10/030016  
DATED : February 14, 2006  
INVENTOR(S) : Elazar Sonnenschein, Minelu Sonnenschein and Randal B. Chinnock Page 1 of 1

It is certified that error appears in the above-identified patent and that said Letters Patent is hereby corrected as shown below:

In the Claims

In Column 15, Claim 1, line 1, change "sheath" to -- shaft --.

Signed and Sealed this  
Ninth Day of July, 2013

Teresa Stanek Rea  
*Acting Director of the United States Patent and Trademark Office*